United States Patent [19]

Lavarenne

[11] Patent Number: 4,822,333

[45] Date of Patent: Apr. 18, 1989

[54] URETHRAL ENDOPROSTHESIS

[76] Inventor: Vincent A. Lavarenne, 13 Av Bolviller, 91800 Brunoy, France

[21] Appl. No.: 92,384

[22] Filed: Sep. 2, 1987

[51] Int. Cl.$^4$ ............................................. A61M 25/00
[52] U.S. Cl. ............................... 600/30; 128/DIG. 25; 604/256; 623/12
[58] Field of Search ........................ 604/104, 105, 256; 128/DIG. 25, 1 R; 623/12; 600/29–32

[56] References Cited

U.S. PATENT DOCUMENTS

| | | | |
|---|---|---|---|
| 3,331,371 | 7/1967 | Rocchi et al. | 128/DIG. 25 |
| 3,503,400 | 3/1970 | Osthagen et al. | 128/DIG. 25 |
| 4,350,161 | 9/1982 | Davis, Jr. | 604/256 |

FOREIGN PATENT DOCUMENTS

| | | | |
|---|---|---|---|
| 0158107 | 10/1985 | European Pat. Off. . | |
| 2450804 | 4/1976 | Fed. Rep. of Germany | 604/256 |
| 2251302 | 6/1975 | France . | |
| 2312264 | 12/1976 | France | 604/256 |
| 2551656 | 9/1986 | France . | |

Primary Examiner—Dalton L. Truluck
Attorney, Agent, or Firm—Browdy and Neimark

[57] ABSTRACT

A urinary catheter forming a continent urethral endoprosthesis equipped with an artificial sphincter which is devoid of an exterior device. The prosthesis includes a tubular body having one end open and having at the other end a seat placed inside the bladder, with a valve urged elastically into the closed position, the seat of which is formed by the other end of the tubular body.

7 Claims, 2 Drawing Sheets

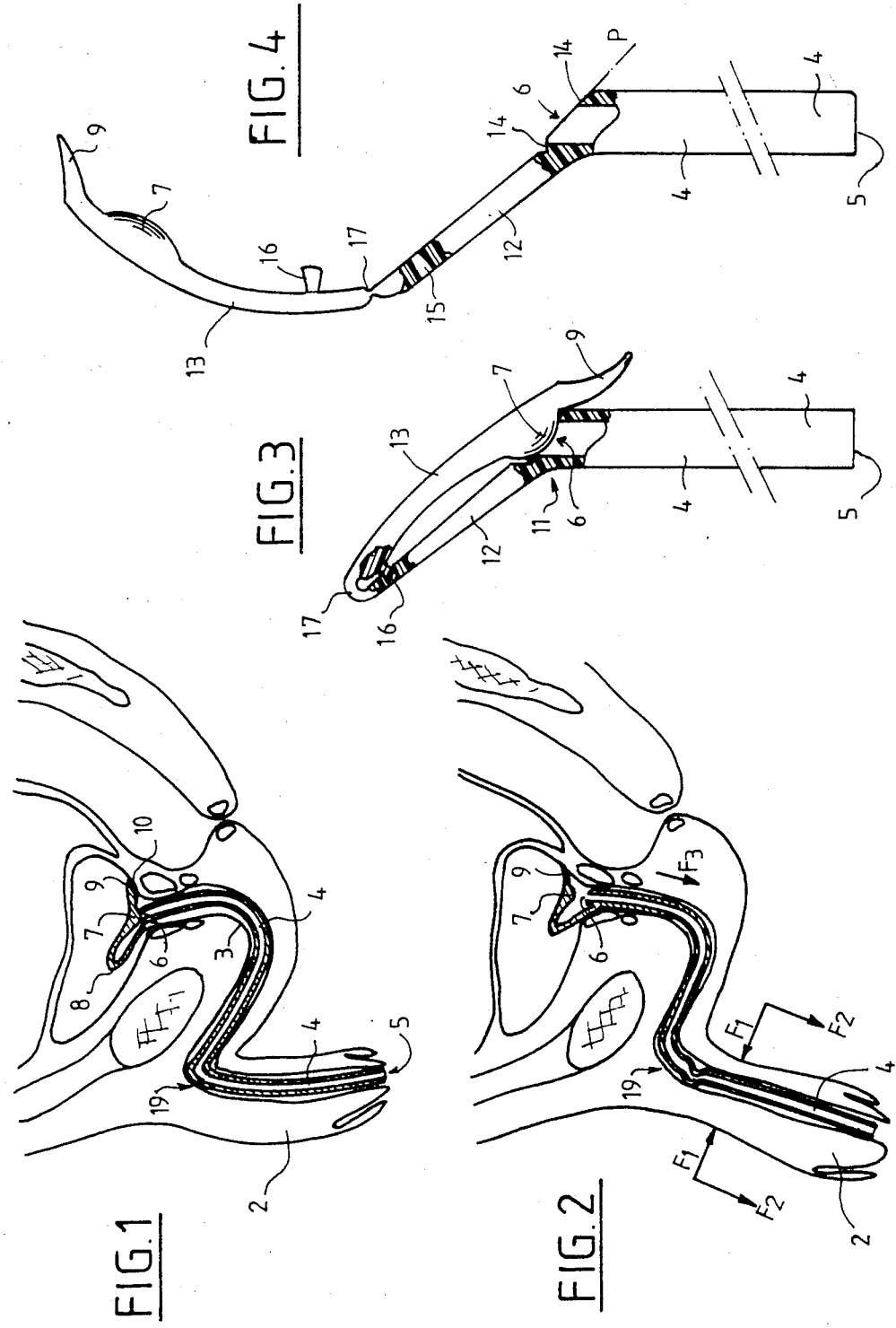

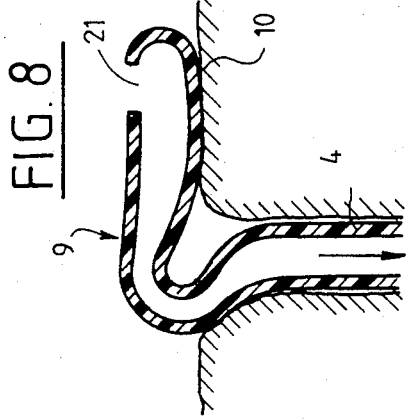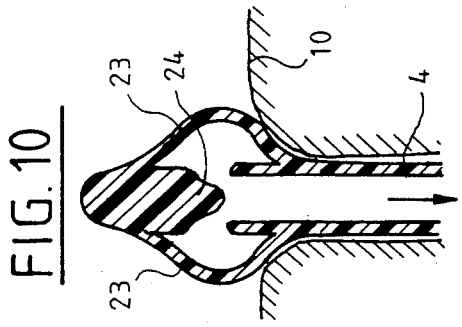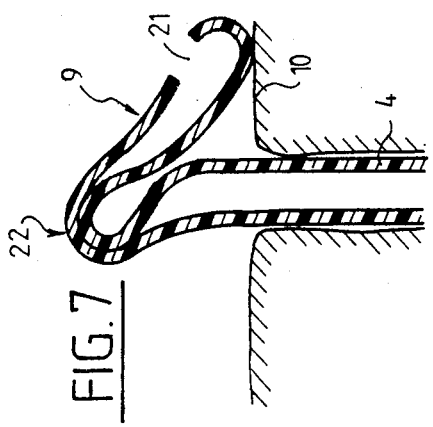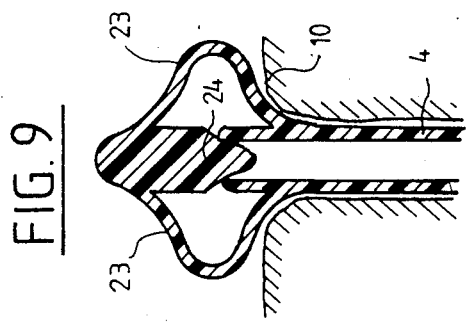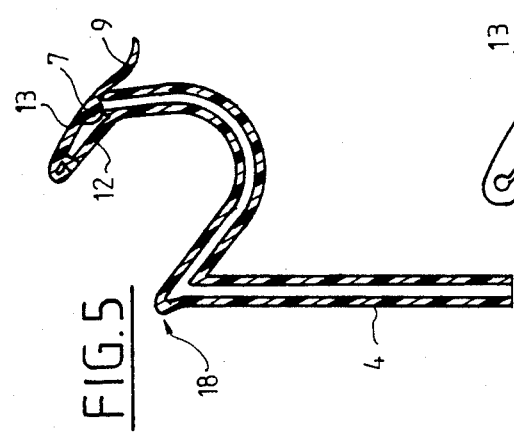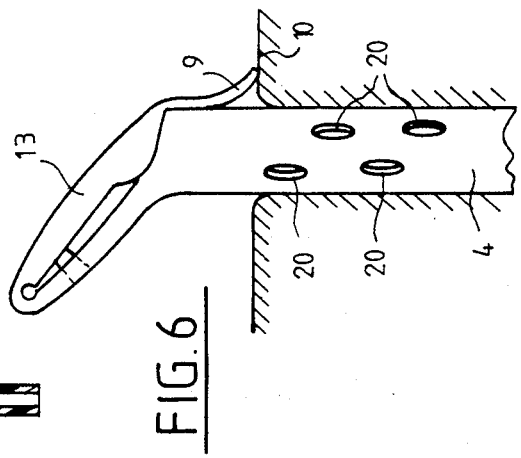

URETHRAL ENDOPROSTHESIS

BACKGROUND OF THE INVENTION

The present invention relates to an improved urinary catheter forming a continent urethral endoprosthesis intended for treating certain lesions of the urethra, the prostate or the urinary sphincters.

As is known, in the case of lesions of the above-mentioned kind, it is the practice to apply a urinary catheter, that is to say a flexible tube inserted into the bladder through the urethra in order to drain the urine.

Existing catheters cause discomfort to the patient mainly for two reasons, however: firstly, they protrude from the penis, and secondly they are not continent and must be plugged or to be connected to a urine collector tube. These reasons make them difficult to tolerate by the patient for a prolonged period or permanently.

A non-protruding urinary catheter, or urethral endoprosthesis by analogy with existing esophageal, biliary and like endoprostheses, constitutes an anticipated advance but one which does not exist at present in any practical form.

Indeed it has been difficult heretofore to devise and use a urethral endoprosthesis for the following reasons: either the endoprosthesis is simply a tube open at both ends, devoid of any device or artificial sphincter to ensure continence; in which case it must be placed underneath the striated urinary sphincter if the patient is not to be made incontinent; the prosthesis is therefore difficult to position and moreover is of only limited usefulness for lesions located beneath the sphincter, to the exclusion of the much more frequent lesions located between the sphincter and the bladder, such as disorders of the prostate;

or the prosthesis is rendered continent by means of an artificial sphincter, that is to say by a valve controlled by the patient.

However, such devices have been imagined and consist either of an electromechanically controlled valve, as described in French Pat. No. 73 40 939, or a valve controlled by the transfer of a fluid in a closed circuit, as described in French Pat. No. 83 14 607. These devices are complex in underlying principle and have found no practical application.

SUMMARY OF THE INVENTION

The present invention has for its object overcoming these various drawbacks by providing a urethral endoprosthesis which is equipped with an artificial sphincter which is devoid of an exterior device, easy to place in position and remove, readily tolerated by the patient and furthermore easy and inexpensive to manufacture by reason of its simplicity.

An endoprosthesis according to this invention consists of a tubular body forming the catheter proper, having one end open and having at its other end a head intended to be placed inside the bladder and having a valve urged elastically into the closed position the seat of which is formed by the said other end of said tubular body, which other end is itself extended by an elastic lateral branch a portion of which forms the valving means proper, said valve comprising a flexible lip for bearing against the internal wall of the bladder.

In accordance with this disposition, when the prosthesis is in position the valve is normally applied against its seat with its lip bearing against the wall of the bladder; consequently when the patient squeezes his penis and exerts a longitudinal pull upon it, the effect is to move the seat away from its valve, the latter remaining substantially in a fixed position, and the permit urination. When the penis is released, the elasticity of its tissues and of the flexible lip returns the valve into its normally closed position.

BRIEF DESCRIPTION OF THE DRAWINGS

Further characteristics and advantages of the invention will become more clearly apparent from the description which follows with reference to the accompanying drawings in which:

FIGS. 1 and 2 schematically illustrate the concept of the endoprosthesis according to the invention, in the normally closed position and the open position respectively;

FIG. 3 depicts a preferred form of embodiment of the endoprosthesis ready to be placed in position.

FIG. 4 shows the endoprosthesis according to FIG. 3 just after manufacture.

FIG. 5 shows a more readily adaptable anatomically-shaped prosthesis.

FIG. 6 is a partial view of a prosthesis enabling sperm to be ejected; and

FIGS. 7 through 10 are schematic illustrations of other possible forms of embodiment of prostheses, shown respectively in the closed position (FIG. 7, FIG. 9) and the open position (FIG. 8, FIG. 10).

In the drawings, like reference numerals refer to like parts.

DESCRIPTION OF THE PREFERRED EMBODIMENTS

Referring first to FIGS. 1 and 2, the bladder 1 is linked to the penis 2 by the urethra 3 inside which is placed the tubular body 4 of the prosthesis. The first end 5 of the tubular body is open and does not protrude from the penis. The second end of the tubular body forms a circular seat 6 for a valve 7 connected through the agency of an elastic lateral branch 8 to the second end of the tubular body. The valve 7 further includes, on the side remote from its attachment to branch 8, a lip 9 placed to bear against the bladder wall 10.

In the inoperative configuration, valve 7 is urged against its seat 6 in a stable closed position in response to the elasticity of branch 8 and no flow occurs from the bladder to the urethra. In fact it should be noted that leaktightness between the urethra 3 and tubular body 4 is ensured by the inherent elasticity of the tissues surrounding said body 4.

All the patient needs to do to bring the prosthesis into the open position to allow urine to flow is to squeeze the penis as shown by the arrows F1 in order to prevent any slipping of the catheter body 4 relative to the urethra 3, and to simultaneously exert a longitudinal pull in the direction of arrows F2. This causes seat 6 to separate from valve 7 in the direction of arrow F3 and, with said valve remaining in a substantially fixed position in pressure contact with wall 10 through its lip 9, flow can take place from the bladder towards the end 5 of the catheter.

Relaxing the pull F2 causes the seat 6 to be urged back into contact with valve 7 by the elasticity of lateral branch 8 and the flexibility of lip 9.

Referring next to FIG. 3, the prosthesis according to the invention ready for positioning shown thereon includes the tubular body 4 with its open end 5 of appropriate length and a valve-forming head, designated overall by reference numeral 11, comprising the lateral branch in two sections 12, 13 folded upon each other, the terminal section 13 incorporating a valve-forming wad 7 and terminating in the lip 9. Although the lateral branch could manifestly be made in a single section instead of two, the illustrated form is preferable for manufacturing reasons as will be more clearly explained with reference to FIG. 4.

The other end of tubular body 4 remote from open end 5 forms the seat 6 in FIGS. 1 and 2. It should be noted however that this seat lies in a plane P (FIG. 4) which forms with the longitudinal axis of body 4 an appropriate angle substantially matching the angle formed anatomically between the urethra axis and wall 10, at the level of said wall. Accordingly, section 12 of the lateral branch is oriented substantially along this plane P. Preferably, the edge 14 of the seat for a sharp angle in order to better ensure leaktightness in the stable closed position of valve 7.

The end of section 12 remote from seat 6 is formed with a hole 15 into which is lockingly engaged a point 16 borne by section 13, this arrangement contributing to urge the valve 7 against its seat in its stable closed position.

Referring now to FIG. 4, the two sections 12 and 13 are interconnected through a thinned-down portion 17 to permit folding, the entire prosthesis being made of a one-piece flexible plastic material of so-called food engineering grade, that is to say compatible with the tissues with which it is intended to be in contact. Preferably, the point 16 is of frusto-conical shape, as well known per se, for securely fastening into hole 15, said hole having a preferably complementary shape. As indicated hereinabove, forming the lateral branch in two sections provides greater elasticity than with a single section and at the same time allows easy molding during manufacture.

Referring next to FIG. 5, the urethral prosthesis shown thereon is an embodiment as shown in FIGS. 3 and 4 and comprises like parts. However, in order to make it easier to tolerate and ensure better retention in position, it may be more closely matched anatomically, with most notably a bend 18 corresponding to the anatomical configuration of the peno-scrotal angle (reference numeral 19 in FIGS. 3 and 4) of the urethra.

It should be noted that the prosthesis according to this invention is tolerated by the patient to the extent of not hindering his ability to have an erection, and accordingly it is possible to provide openings 20 (FIG. 6) in that part of tube 4 which is to be positioned level with the prostatic urethra, thereby to permit discharging of sperm.

In accordance with the underlying concept of the invention and with reference to FIGS. 7 through 10, the seat/valve combination of the prosthesis can take different forms, the principle of operation remaining as described precedingly. In accordance with FIGS. 7 and 8, the seat and valve can be formed without a break in continuity, in which case that end of tube 4 which is to be positioned inside the bladder is bent to form the lip 9, which lip is accordingly provided with an opening 21 leading into the bladder. The elasticity of the material is by design such as to permit, in the normal resting or closed position, a squeezing 22 of the two walls of the tube whereby to perform the function of a seat/valve combination which provides an open position by traction (FIG. 8). In an alternative embodiment shown in FIG. 9, the flexible lip is formed of two symmetrical branches 23 and embodies a valve-forming wad 24 opposite the end 6 of tube 4. As in the previously described embodiment, exerting a pull disengages the wad from the valve seat to provide the open position (FIG. 10).

It goes without saying that the present invention is by no means limited to the embodiments described with reference to the accompanying drawings and that many changes and substitutions may be made without departing from the spirit and scope of the invention.

What is claimed is:

1. A urethral endoprosthesis comprising a tubular body forming a urinary catheter in the urethra and having a first end which is open and intended to be located at the tip of the penis without protruding therefrom, valving means integral with said tubular body intended to be positioned within the bladder, at the second end of said tubular body, said valving means being elastically urged into a closed position;

a flexible and elastic portion of said valving means being applied against the internal wall of the bladder whereby to close said valving means in the rest position and to open it when the tubular body is pulled by squeezing the penis.

2. A urethral endoprosthesis as claimed in claim 1, in which the valving means include a valve elastically urged into a closed position on a seat, said seat being formed by said second end of the tubular body, in a plane which forms with the axis of said tubular body an angle substantially equal to the angle which the urethral axis forms, on the level of the internal wall of the bladder, with said internal wall;

said end prosthesis further including:

a lateral elastic branch extending said open end of the tubular body, formed with first and second sections joined by a thinneddown portion and foldable upon each other, the second terminal section incorporating said valve in the form of a wad;

a flexible lip extending said terminal section, adapted to bear against the internal wall of the bladder;

a hole formed in said first section, in proximity to said thinned-down portion, and a point carried on said second section and adapted to engage into said hole.

3. An endoprosthesis as claimed in claim 1, in which that part of the tubular body which is to be positioned in the prostatic urethra is formed with openings therein.

4. An endoprosthesis as claimed in claim 1, in which said tubular body is formed with a bend anatomically matching the peno-scrotal angle of the urethra.

5. An endoprosthesis as claimed in claim 1, in which the valving means are formed by said second end of said tubular body, said valving means being in the form of a bend forming said elastic portion and provided with an opening therein, said valving means having a seat/valve combination formed by a pinching of the tube at the level of said bend.

6. An endoprosthesis as claimed in claim 1, in which said flexible elastic portion is formed by two symmetrical branches and the valving means include a seat formed by said second end of said tubular body, a wad provided between said symmetrical branches being elastically applied against said seat.

7. An endoprosthesis as claimed in claim 1, formed in a one-piece molding of a plastic material compatible with the tissues with which it is intended to be in contact.

* * * * *